(12) United States Patent
Carr

(10) Patent No.: US 7,699,841 B2
(45) Date of Patent: Apr. 20, 2010

(54) MICROWAVE APPARATUS FOR CONTROLLED TISSUE ABLATION

(75) Inventor: Kenneth L. Carr, Woolwich, ME (US)

(73) Assignee: Meridian Medical Systems, LLC, Woolwich, ME (US)

( * ) Notice: Subject to any disclaimer, the term of this patent is extended or adjusted under 35 U.S.C. 154(b) by 1070 days.

(21) Appl. No.: 11/377,789

(22) Filed: Mar. 16, 2006

(65) Prior Publication Data

US 2007/0219548 A1 Sep. 20, 2007

(51) Int. Cl.
*A61B 18/18* (2006.01)
(52) U.S. Cl. .............................. 606/33; 606/41; 607/156
(58) Field of Classification Search ............. 606/32–52; 607/154–156
See application file for complete search history.

(56) References Cited

U.S. PATENT DOCUMENTS

| | | | | |
|---|---|---|---|---|
| 4,154,246 A | * | 5/1979 | LeVeen | ........................ 607/99 |
| 4,557,272 A | * | 12/1985 | Carr | ........................... 600/549 |
| 4,583,556 A | | 4/1986 | Hines et al. | |
| 5,186,171 A | * | 2/1993 | Kuhry | ......................... 607/68 |
| 5,364,336 A | | 11/1994 | Carr | |
| 5,531,662 A | | 7/1996 | Carr | |
| 5,683,382 A | * | 11/1997 | Lenihan et al. | ............... 606/33 |
| 5,690,614 A | | 11/1997 | Carr et al. | |
| 5,800,494 A | * | 9/1998 | Campbell et al. | ........... 607/116 |
| 6,051,018 A | * | 4/2000 | Larsen | ........................ 607/96 |
| 6,496,738 B2 | | 12/2002 | Carr | |
| 6,932,776 B2 | | 8/2005 | Carr | |
| 2004/0249272 A1 | | 12/2004 | Carr | |
| 2005/0228370 A1 | * | 10/2005 | Sterzer et al. | ................. 606/33 |

* cited by examiner

*Primary Examiner*—Linda C Dvorak
*Assistant Examiner*—Ronald Hupczey, Jr.
(74) *Attorney, Agent, or Firm*—Cesari and McKenna, LLP

(57) ABSTRACT

Apparatus for controlled tissue ablation includes an elongated relatively flexible antenna with a first, strip-like, conductor having opposite faces and proximal and distal ends, a dielectric spacer covering one face of the first conductor, and a second, serpentine, conductor composed of a series of similar segments positioned flush against the spacer and being coextensive lengthwise with the first conductor. The second conductor has a distal end connected to the distal end of the first conductor and a proximal end. An electrically insulating enclosure surrounds the conductors. The proximal ends of the first and second conductors may be connected via a coaxial cable to a remote microwave transmitter/receiver unit.

21 Claims, 4 Drawing Sheets

MICROWAVE APPARATUS FOR CONTROLLED TISSUE ABLATION

BACKGROUND OF THE INVENTION

1. Field of the Invention

This invention relates to a microwave apparatus for controlled tissue ablation. It relates especially to such apparatus which incorporates a minimally invasive microwave antenna catheter which can transmit and receive signals at different frequencies.

It is well known in the medical field to transmit electromagnetic energy to internal tissue by way of an antenna placed close to the tissue in order to heat the tissue sufficiently to ablate or necrose same by hyperthermia. Invariably the antenna is incorporated into a catheter which can be inserted into the body and positioned near the tissue of interest. In many cases, catheter ablation of tissue is the preferred treatment for cardiac arrhythmia.

2. Description of the Prior Art

Heretofore, various antenna types have been used for ablation/necrosis treatment applications. These include monopole, dipole and helical antennas as well as capacitor tip antennas. See, for example, my U.S. Pat. Nos. 4,583,556, 5,683,382 and 6,932,776. Although those prior antennas and the apparatus associated therewith are certainly capable of heating tissue, they are not particularly suitable for carrying out minimally invasive procedures such as the ablation of heart tissue. This is because the prior antennas are relatively large and stiff making it difficult to place the antenna in the position necessary to treat the problem of cardiac arrhythmias. Such treatment usually requires that the antenna be placed close to one of the major blood vessels where it connects to the heart and to deliver a uniform, predictable and controllable heating pattern to ablate or necrose tissue in the vessel wall that will produce a lesion of just the right size to treat the arrhythmias.

Also, the antenna catheters commonly used for this purpose do not monitor the actual temperature of the tissue being heated by the catheter. At most, they may incorporate a thermister or thermocouple in the catheter tip that is used to control the output of the transmitter that produces the microwave energy radiated by the antenna. However, those devices simply sense the temperature at the catheter, not the actual temperature of the tissue being treated. This can result in the tissue being underheated in which case the procedure will take longer than it should, or being overheated resulting in unintended damage to the tissue adjacent to the desired lesion.

SUMMARY OF THE INVENTION

Accordingly, it is an object of the present invention to provide an improved microwave apparatus for producing controlled tissue ablation.

Another object of the invention is to provide such apparatus which includes a minimally invasive antenna catheter that is particularly suitable for treating cardiac arrhythmias.

Still another object of the invention is to provide apparatus such as this which is capable of heating tissue in a controlled manner.

A further object of the invention is to provide a minimally invasive microwave antenna particularly adapted to ablate or necrose tissue at or near the heart.

A further object of the invention is to provide such an antenna which can operate over a large frequency range.

A further object of the invention is to provide a microwave antenna which can simultaneously transmit and receive signals having substantially different frequencies.

Still another object of the invention is to provide an antenna catheter which has an elongated uniform antenna pattern which can be directed toward the tissue being treated.

A further object of the invention is to provide an antenna catheter having one or more of the above characteristics and which can be made relatively inexpensively using known etched or printed circuit techniques.

Other objects will, in part be obvious, and will, in part, appear hereinafter.

The invention accordingly comprises the features of construction, combination of elements and arrangement of parts which will be exemplified in the construction hereinafter set forth, and the scope of the invention will be indicated in the claims.

In general, my apparatus for controlled tissue ablation comprises an elongated flexible antenna including a first, strip-like, conductor having a proximal end and a distal end and a second, serpentine conductor, composed of a series of similar segments and having a distal end connected to the distal end of the first conductor and a proximal end. Preferably, the second conductor segments are wider than the first conductor so that those segments overhang the sides of the first conductor. A dielectric spacer is interposed between the second conductor segments and the first conductor to electrically isolate same. Preferably also, the first and second conductors as well as the spacer are enclosed within an electrically insulating enclosure so that the antenna conductors cannot directly contact the tissue of a patient being treated.

In use, a microwave transmitter/receiver unit is connected by way of the inner and outer conductors of a coaxial cable to the proximal ends of the first and second conductors, respectively. The transmitters/receiver unit includes a microwave transmitter which transmits a heating signal at a first frequency to the antenna via the cable which causes the antenna to radiate energy in a uniform pattern capable of heating tissue adjacent to the antenna. The antenna is designed to operate over a wide frequency range so that it can simultaneously detect much higher frequency emissions from the tissue being treated which signal is a direct indication of the temperature of that tissue. The temperature-indicating measuring signal is applied via the cable to the transmitter/receiver unit which includes a radiometer whose output provides a real time indication of the tissue temperature.

As we shall see, the transmitter/receiver unit also includes a diplexer which prevents the heating signal from being applied to the radiometer and also prevents the measuring signal from being coupled to the transmitter. The transmitter/receiver unit may also include a processor which responds to the output of the radiometer to apply a control signal to the transmitter causing the antenna to heat the adjacent tissue in a controlled manner. Thus the apparatus as a whole is able to controllably heat the tissue and provide a direct indication of the temperature of the tissue being heated. This enables the apparatus to be placed in proximity to the tissue being treated and to ablate or necrose that tissue to produce a lesion of just the right size, e.g. to treat a cardiac arrhythmia.

In a preferred embodiment of the invention, the antenna enclosure comprises a housing having a portion adjacent to the first conductor made of a material having a low dielectric constant. Thus, when the second conductor is placed in close proximity to a high dielectric material such as tissue which has a relatively high water content, the antenna pattern will be directed toward that tissue. Such a dielectric enclosure thus increases the heating efficiency of the apparatus and optimizes its ability to detect small changes in the temperature of the tissue being heated.

BRIEF DESCRIPTION OF THE DRAWINGS

For a fuller understanding of the nature and objects of the invention, reference should be made to the following detailed description taken in connection with the accompanying drawings, in which.

DETAILED DESCRIPTION OF AN ILLUSTRATIVE EMBODIMENT

Figure 1:
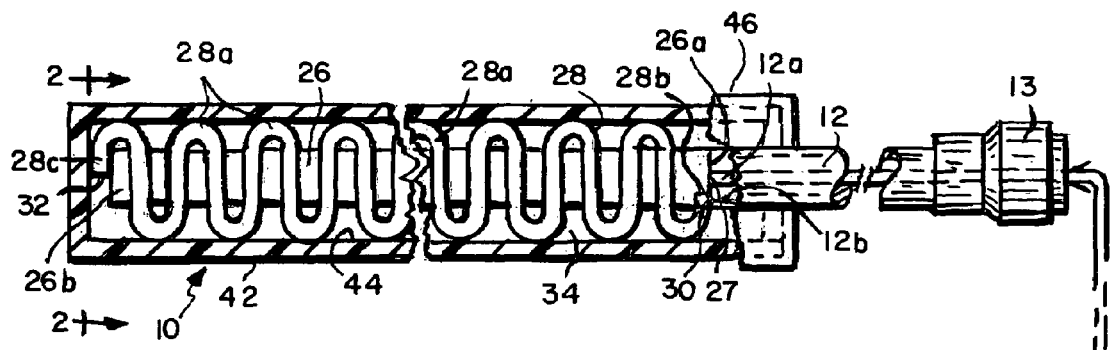
FIG. 1 is a plan view with some parts shown in schematic form and other parts in block form of microwave apparatus for controlled tissue ablation according to the invention.
Figure 1:
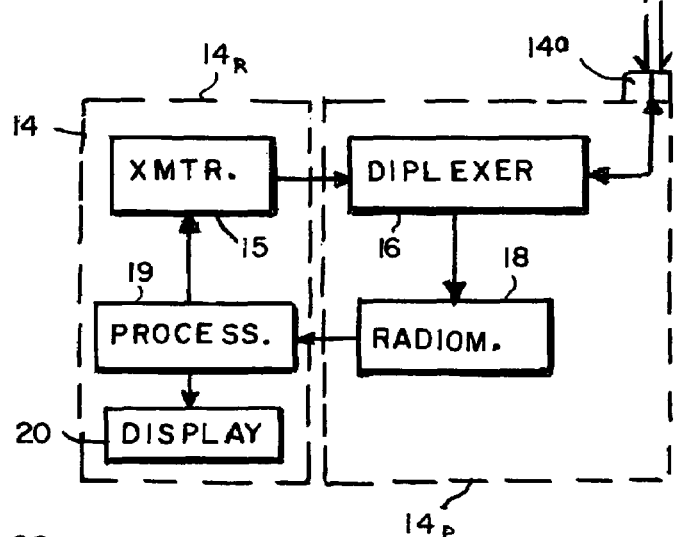

Referring to FIG. 1 of the drawings, my apparatus comprises a microwave antenna catheter shown generally at 10 which includes a co-axial cable 12 terminated by a connector 13 which is adapted to be coupled to the connector 14a of a remote transmitter/receiver unit 14.

Unit 14 includes a microwave transmitter 15 which transmits a signal at a first frequency approved by the Federal Communications Commission, e.g. 2450 or 915 MHz, via a diplexer 16 to catheter 10. This causes the antenna to radiate electromagnetic energy in a pattern capable of heating tissue adjacent to the catheter. The antenna catheter 10 also detects thermal radiation emitted by that tissue and applies a corresponding measuring signal via cable 12 to the diplexer 16. The diplexer routes that signal to a radiometer 18 in unit 14. The radiometer operates at a center frequency in the order of 1 to 4 GHz so that the apparatus can detect thermal emissions from locations relatively deep in the tissue being treated. The output of radiometer 18 is processed by a processor 19 in unit 14 which controls a display 20 therein.

The diplexer 16 and the other elements in unit 14 are known and not part of this invention. Suffice it to say here that the diplexer 16 isolates the radiometer 18 from the signal being transmitted by transmitter 15 to the antenna catheter 10 and isolates the transmitter 15 from the temperature-indicating signal from catheter 10 being routed to the radiometer 18. The processor 19 receives the signal from radiometer 18 and uses that signal to control transmitter 15 so that the antenna catheter radiates sufficient energy to maintain the adjacent tissue at a selected temperature. The processor 19 may also control display 20 to display a variety of different parameters such as tissue temperature, transmitter frequency, output power, reflected power, elapsed time, etc. In FIG. 1, all of the external elements of the apparatus are shown in a single unit 14. It should be understood that the diplexer 16 and radiometer could be placed in a small subunit $14_p$ proximal to the catheter 10 implanted in a patient to minimize losses and signed errors due to the coaxial cable, while the other external elements may be placed in a remote subunit $14_R$ far removed from the patient.

Figure 2:
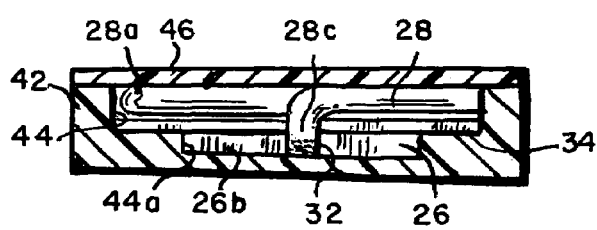
FIG. 2 is a sectional view on a larger scale taken along line 2-2 of FIG. 1.

As best seen in the FIGS. 1 and 2, the antenna catheter 10 comprises a first elongated conductor 26 having a proximal end 26a and a distal end 26b. Preferably, the conductor is in the form of a flat metal strip having a generally rectangular cross section as shown. The cable 12 includes an inner conductor 12a which is connected to the proximal end 26a of first conductor 26 via a weld or solder bead 27.

Antenna catheter 10 also includes a second conductor 28 in the form of a serpentine wire that overlies conductor 26 and is lengthwise coextensive therewith. Thus conductor 28 is made up of a series of sinuous segments or cycles 28a which extend laterally beyond the side edges of conductor 26. The proximal end 28b of conductor 28 is connected to an outer conductor 12b of cable 12 via a solder or weld bead 30.

As best seen in FIG. 2, the distal end 28c of conductor 28 overlaps the distal end 26b of conductor 26 and those two ends are connected together by a weld bead 32. Thus, the conductor 26 is returned to ground via conductor 28 and the cable conductor 12b to assure patient safety.

Between their ends, the conductors 26 and 28 are electrically insulated from one another by a dielectric spacer 34 of a material having a low dielectric constant and a low loss tangent and which preferably, but not necessarily, extends the full width of the conductor segments 28a as shown in FIG. 2. A suitable spacer material is PTFE or silicone.

In a catheter 10 exemplar, the conductor 26 may be a 0.060×0.030 mm rectangular rod, the conductor 28 may be a 0.020 mm diameter wire, the insulating spacer 34 may be a 0.008 mm PTFE film and cover 46 may be a 0.005 mm film of the same material. The illustrated catheter 10 has an antenna length, i.e. the distance between conductor ends 28a and 28b, of 4 cm with the conductor segments 28a having a width of 0.016 mm, a spacing between adjacent segments of 16 mm, and a lateral overhang of 0.40 mm.

Desirably the antenna conductors 26 and 28 are electrically insulated from the patient. This may be accomplished by placing the conductors within an electrically insulating enclosure 42. The enclosure may be a flexible envelope or encapsulation of a dielectric material. More preferably, the enclosure 42 is, as shown, a box-like housing of a low dielectric material such as aerated PTFE or silicone and formed with a recess 44 which is wide and deep enough to accommodate the conductor segments 28a and the dielectric spacer 34, and with a slightly deeper axial recess extension 44a (FIG. 2) to receive conductor 26. The opening into recess 44 may be closed by a cover 46 consisting of a thin sheet of dielectric material, e.g. PTFE, which may be adhered to the top of enclosure 42.

Figure 4:
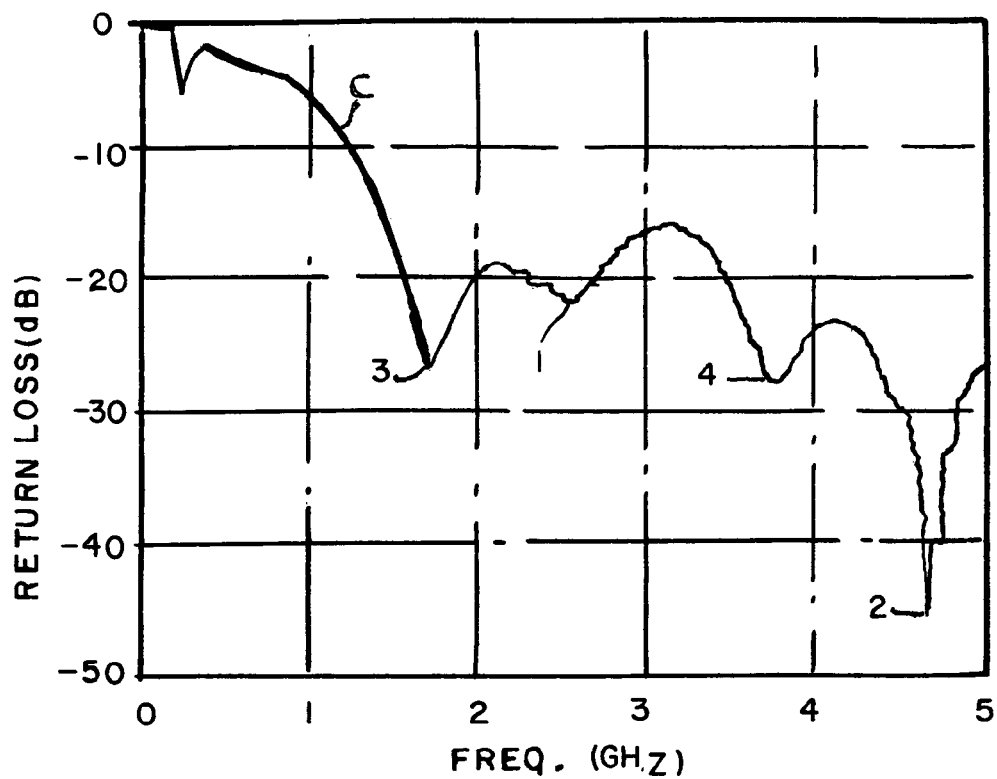
FIG. 4 is a graphical diagram showing the return loss of the antenna in FIG. 1 over a range of frequencies.

Since the present apparatus provides a heating signal at a first frequency e.g. 2450 MHz (2.45 GHz), and detects thermal emissions at a second widely different frequency, e.g. 4 GHz, the antenna catheter 10 must operate over a wide frequency range allowing use at multiple frequencies with a good impedance match at those frequencies FIG. 4 is a graph plotting the return loss or reflection coefficient of the above catheter exemplar across a range of frequencies. The curve C allows one to determine if the antenna is reasonably "matched" to the desired frequencies. To obtain the curve C, a network analyzer sends a small amount of energy to antenna catheter 10 at a number of different frequencies from 0-5 GHz and records the amount of energy that returns. The recorded energy levels are shown on a graph of energy level (in dB) versus frequency (in GHz). The graph starts at 0 dB and the lesser the return energy, the more negative the curve C. A well matched antenna should have a return loss less than 20 dB.

As can be seen from FIG. 4, curve C has relatively small dB numbers at the 2.45 GHz heating frequency (point 1) and the 4.0 GHz measuring frequency (between points 2 and 4), indicating that the antenna catheter is reasonably well matched at those frequencies. Ideally, the catheter 10 should be matched to operate at or near one of the points 1-4 of minimal energy return on curve C which points occur at regular intervals along the curve.

Figure 5:
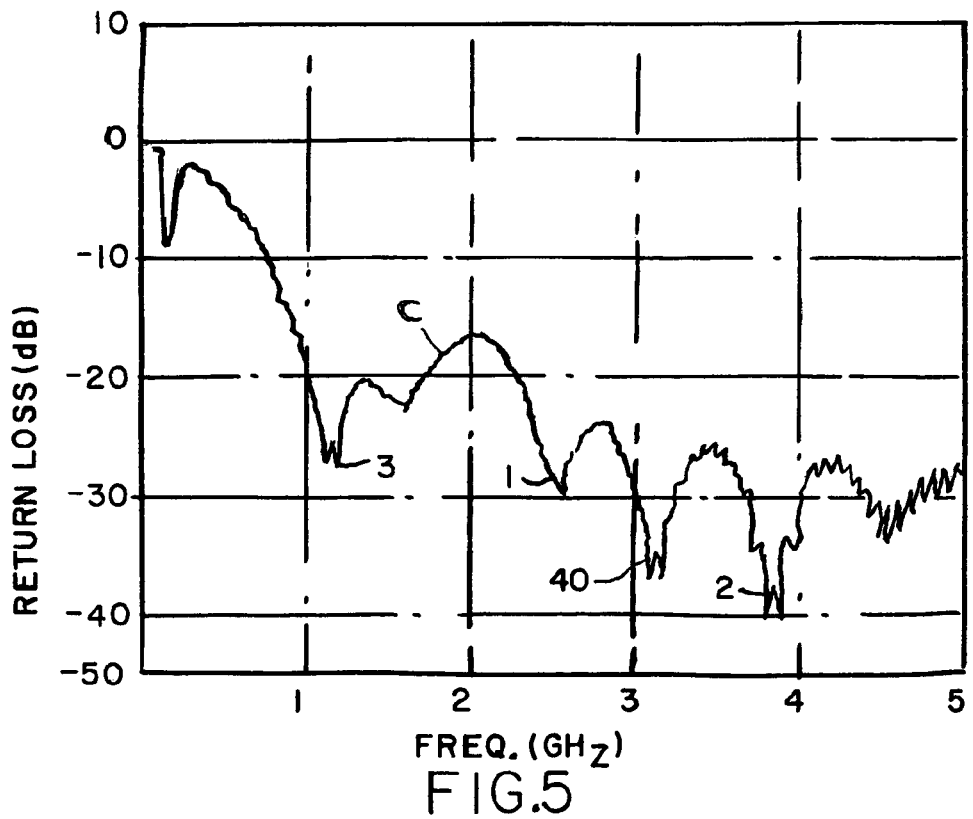
FIG. 5 is a similar graph of the return loss of a longer antenna.

A major factor influencing the position of the minimum curve points in the frequency spectrum is the length of the antenna catheter 10. When antenna length is increased by increasing the number of sections 28a in conductor 28 (and lengthening conductor 26 correspondingly) the negative points 1 to 4 in curve C are shifted to the left in FIG. 4. This is apparent from a comparison of FIG. 4 with FIG. 5 which is a graph showing the return loss for an antenna that is 6 cm, vs. 4 cm, long with a 5 mil. spacer 34. The is opposite effect may be obtained by shortening the antenna.

Also, changing the cross-sections of conductors 26 and 28 and the thickness of the spacer 34 and the spacing of the conductor 28a segments similarly affects the frequency of the antenna. Therefore, once the catheter 10 length has been selected, one or another of the above antenna parameters may be varied to provide an antenna catheter which operates with maximum efficiency at the desired heating and measuring frequencies.

Figure 6B:
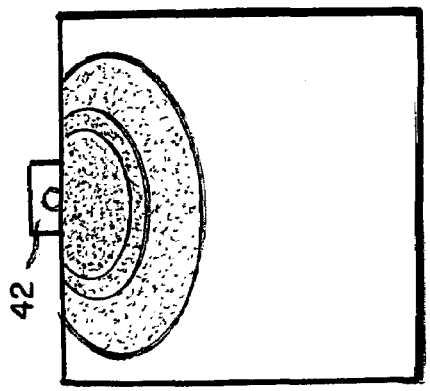
FIGS. 6A and 6B are, respectively, longitudinal and cross-sectional views of the antenna pattern of the antenna in FIG. 1 at a selected heating frequency.
Figure 7B:
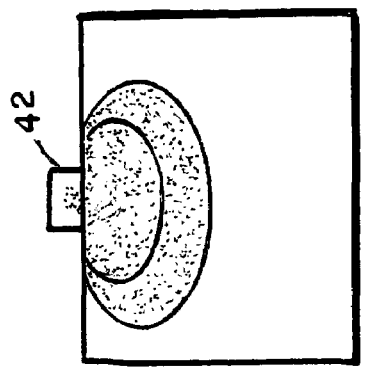
FIGS. 7A to 7B are, respectively, similar views of the antenna pattern of that antenna at a selected measuring frequency.
Figure 6A:
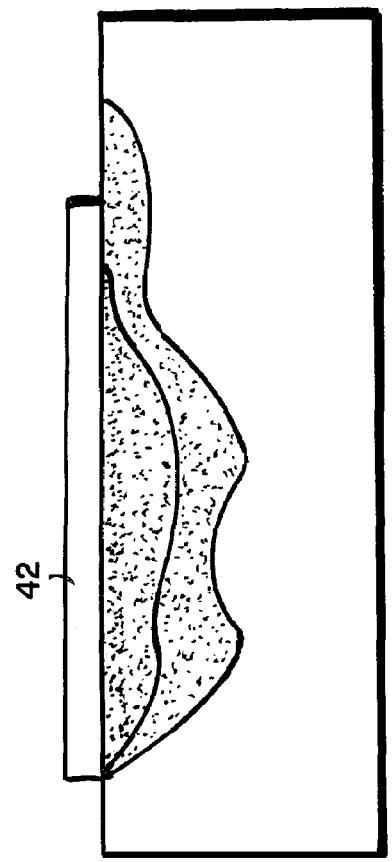
Figure 7A:
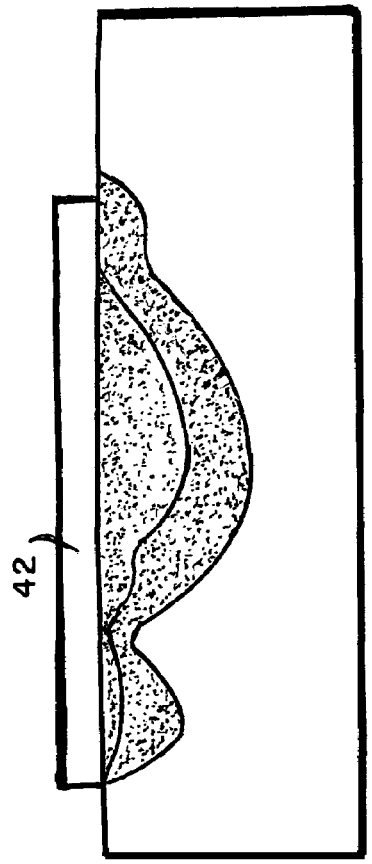

FIGS. 6A and 6B illustrate longitudinal and cross-sectional views respectively of the antenna pattern of catheter 10 operated at a heating frequency of 2.45 GHz. FIGS. 7A and 7B are similar views of the antenna pattern of catheter 10 operated at a frequency of 4.0 GHz. It should be noted that antenna patterns are usually obtained in the transmit or radiate mode rather than the receive mode. However, reciprocity dictates that the two patterns be identical. In any event, it is readily apparent from these figures that the antenna patterns for both the heating and measuring frequencies are relatively uniform along the catheter and are directed uniformly away from the cover 46; i.e. toward the tissue being treated.

Figure 8:
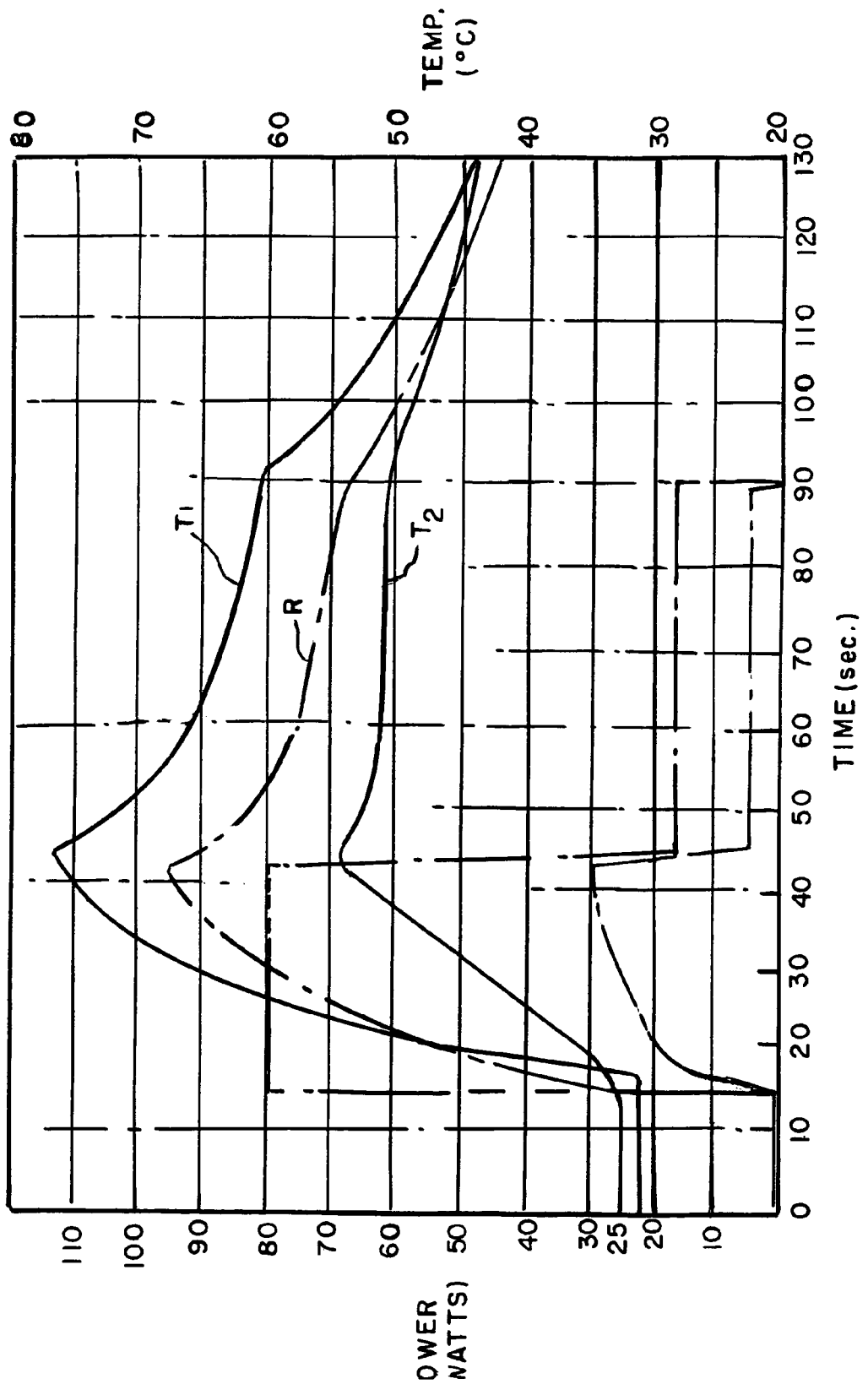
FIG. 8 is a graphical diagram illustrating the operation of the FIG. 1 apparatus.

FIG. 8 is a graph demonstrating the actual performance of catheter 10 during simultaneous heating and measuring of tissue placed opposite the catheter. In this example, power at 80 Watts and 2.45 GHz is applied to the catheter at time 15 seconds and held for 30 seconds at which time the power is reduced to 20 Watts. Radiometric data is then taken represented by curve R, along with temperature data from conventional Luxtron probes placed in the tissue, represented by curves $T_1$ and $T_2$. As seen from FIG. 8, the radiometric data are quite consistent with the temperatures measured by the probes imbedded in the tissue indicating that the subject apparatus provides an accurate real time measurement of the actual temperature of the tissue being treated.

When, as shown in FIGS. 1 and 2, the enclosure 42 is in the form of a housing made of a material having a low dielectric constant such as silicone, aerated PTFE and the like, the antenna has a directional antenna pattern. That is, when the antenna conductor 28 is placed in close proximity to tissue which has a relatively high water content and thus a relatively high dielectric constant, the microwave energy from the antenna will be directed into that tissue. Thus unlike the case with some prior catheters of this general type, no reflective shield is required which could reduce the overall flexibility of the antenna catheter. In other words, the present catheter has minimal or no field coupling in the direction away from the tissue being ablated. This feature improves both the safety and efficiency of the apparatus. It also makes it safe for the surgeon to handle and manipulate, i.e. he/she is less apt to suffer radiation burns.

Figure 3:
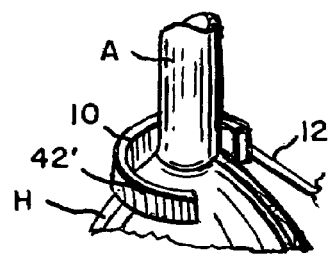
FIG. 3 is a perspective view on a much smaller scale showing the present apparatus used to treat cardiac arrhythmias.

It will be appreciated from the forgoing that antenna catheter 10 has several distinct advantages. More particularly, its conductors 26 and 28 can be made quite thin using conventional printed or etched circuit techniques thereby minimizing manufacturing cost. Also, as shown in FIG. 3, when those conductors are encased within a flexible enclosure 42, such as a plastic envelope 42', the overall antenna catheter is flexible enough so that during a surgical procedure to treat a cardiac arrhythmia, it can be positioned around an artery A close to the heart H of a patient. Since the antenna conductor 28 is returned to ground and the antenna as a whole is electrically isolated by its enclosure from the tissue to be heated, the antenna should satisfy all FDA safety requirements.

It will thus be seen that the objects set forth above, among those made apparent from the preceding description, are efficiently attained. Also, since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention described herein.

The invention claimed is:

1. Apparatus for tissue ablation, said apparatus comprising
    an elongated catheter terminated by a relatively flat antenna having opposite faces and including
    a first, linear, conductor having opposite faces and proximal and distal ends,
    an electrically insulating spacer covering one face of the first conductor, and
    a second, serpentine, conductor composed of a series of similar segments positioned flush against said spacer and being coextensive lengthwise with the first conductor, said second conductor having a distal end connected to the distal end of the first conductor and a proximal end, and
    an electrically insulating enclosure surrounding the conductors, said enclosure including a body of low dielectric material adjacent the first conductor at one face of said antenna so that the antenna has a characteristic radiation pattern that is directed preferentially away from the other face of the antenna.

2. The apparatus defined in claim 1 wherein the first conductor is a flat strip and the second conductor is a wire.

3. The apparatus defined in claim 1 wherein
    the first conductor is a rectangular strip having opposite sides, and
    said segments of the second conductor overhang the opposite sides of the first conductor.

4. The apparatus defined in claim 1 wherein the spacer is of a low dielectric material.

5. The apparatus defined in claim 1 wherein said catheter includes a coaxial cable having a grounded inner conductor connected to the proximal end of the first conductor, and an outer conductor connected to the proximal end of the second conductor.

6. The apparatus defined in claim 1 wherein the antenna is flexible.

7. The apparatus defined in claim 1 wherein the enclosure comprises
    a housing of a low dielectric material forming said body and defining a recess shaped and arranged to receive the conductors so that the second conductor faces an entrance into the recess, and a low dielectric cover covering said entrance.

8. The apparatus defined in claim 7 wherein the housing is of silicone or aerated PTFE.

9. The apparatus defined in claim 1 and further including a microwave transmitter/receiver unit, and wherein the catheter includes a coaxial cable including an inner conductor having one end connected to the proximal end of the first conductor and another end connected to said unit and an outer conductor having one end connected to the proximal end of the second conductor and another end connected to said unit.

10. The apparatus defined in claim 1 wherein said antenna has an antenna length in the range of 4 to 6 centimeters.

11. The apparatus defined in claim 1 and further including a microwave transmitter, and wherein said catheter includes a coaxial cable connected between said transmitter and said antenna.

12. The apparatus defined in claim 11 wherein said transmitter transmits at a selected frequency in the range of 915 to 2450 MHz, and the antenna is well matched to said selected frequency.

13. The apparatus defined in claim 12 and further including a microwave receiver having a center frequency appreciably different from said selected frequency, and wherein the catheter includes a coaxial cable connected between the receiver and the antenna.

14. The apparatus defined in claim 13 wherein the antenna is well matched to said center frequency.

15. The apparatus defined in claim 1 and further including a microwave transmitter which transmits at a first frequency; a microwave receiver which has a selected center frequency appreciably greater than said first frequency, and said catheter includes a coaxial cable connecting the antenna to the transmitter and receiver, said antenna providing a good impedance match at both the first frequency and the center frequency.

16. Apparatus for tissue ablation, said apparatus comprising an elongated catheter terminated by a relatively flat antenna, said antenna having opposite faces and including a serpentine conductor composed of a series of substantially similar sinuous segments and having proximal and distal ends and a longitudinal axis extending between said ends;

a substantially straight conductor having proximal and distal ends and a longitudinal axis extending therebetween, said conductors being spaced opposite one another with their axes in parallelism so as to provide an insulating gap between said conductors;

a electrical connection between the distal ends of the conductors, and a body of low dielectric material adjacent the straight conductor at one face of the antenna whereby the antenna has a characteristic antenna pattern which is directed preferentially away from the other face of the antenna.

17. The apparatus defined in claim 16 and further including a low dielectric spacer filling the gap between the serpentine and straight conductors.

18. The apparatus defined in claim 16 wherein the straight conductor is a flat strip and the serpentine conductor is a wire.

19. The apparatus defined in claim 18 wherein the straight conductor is a substantially rectangular strip having opposite sides, and said segments of the serpentine conductor overhang the opposites sides of the said rectangular strip.

20. The apparatus defined in claim 16 and further including a low dielectric cover member insulating said conductors from the outside.

21. The apparatus defined in claim 20 wherein the antenna and cover member are flexible.

* * * * *